(12) United States Patent
Lalena et al.

(10) Patent No.: US 8,678,648 B2
(45) Date of Patent: Mar. 25, 2014

(54) MOBILE RADIOGRAPHY UNIT HAVING SINGLE SIGN ON AND METHODS FOR USING THE SAME

(75) Inventors: Michael C. Lalena, Webster, NY (US); Christopher J. Kralles, Rochester, NY (US); Martin E. Trzcinski, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 298 days.

(21) Appl. No.: 13/084,907

(22) Filed: Apr. 12, 2011

(65) Prior Publication Data

US 2012/0093294 A1    Apr. 19, 2012

Related U.S. Application Data (60) Provisional application No. 61/323,535, filed on Apr. 13, 2010.

(51) Int. Cl.
*H05G 1/02* (2006.01)

(52) U.S. Cl.
USPC .......................................... 378/198; 378/114

(58) Field of Classification Search
USPC ........................ 378/114, 115, 116, 197, 198
See application file for complete search history.

(56) References Cited

U.S. PATENT DOCUMENTS

| | | | |
|---|---|---|---|
| 5,844,961 | A | 12/1998 | McEvoy et al. |
| 6,760,755 | B1 | 7/2004 | Brackett |
| 7,103,776 | B1 | 9/2006 | Hall |
| 7,611,282 | B2 | 11/2009 | Koren et al. |
| 2005/0114654 | A1 | 5/2005 | Brackett et al. |
| 2006/0195484 | A1 | 8/2006 | Mahesh et al. |
| 2006/0219776 | A1 | 10/2006 | Finn |
| 2007/0167720 | A1 | 7/2007 | Viswanathan et al. |
| 2008/0205589 | A1 * | 8/2008 | Camus ........................... 378/20 |
| 2008/0314973 | A1 | 12/2008 | Zuhars et al. |
| 2010/0034451 | A1 * | 2/2010 | Hughes .......................... 378/87 |
| 2010/0128991 | A1 | 5/2010 | Weese et al. |
| 2010/0131292 | A1 | 5/2010 | Hawkins et al. |
| 2012/0045037 | A1 * | 2/2012 | Carmichael et al. .......... 378/198 |

FOREIGN PATENT DOCUMENTS

| | | |
|---|---|---|
| EP | 2 273 416 A1 | 1/2011 |
| WO | WO 2007/078684 | 7/2007 |
| WO | WO 2007/139638 | 12/2007 |

* cited by examiner

*Primary Examiner* — Glen Kao

(57) ABSTRACT

A mobile radiography apparatus has a moveable (e.g., wheeled) transport frame and an adjustable column mounted at the frame. A boom apparatus supported by the adjustable column can support an x-ray source and can be coupled to a optional second display (also adjustably mounted). Embodiments of methods and/or apparatus by which mobile radiography carts can provide a single secure access apparatus and/or methods to control at least two of (i) a transport mechanism, (ii) x-ray generator control, (iii) remote detector control and image processing control, or (iv) secured storage for at least one radiographic detector by a single operator action.

20 Claims, 10 Drawing Sheets

| Patient Name | Location | Exam | Exam Time |
|---|---|---|---|
| ● James Johnson | Rm 203 | Portable Chest | 4/11/2010 11:23:51 AM |
| ● Fred Smith | Rm 224 | Knee | 4/11/2010 11:24:12 AM |
| ● Fred Jones | Rm 245 | Portable Chest | 4/11/2010 11:23:44 AM |
| ● Scott Smith | Rm 252 | Portable Hip | 4/11/2010 11:24:05 AM |
| ● John Jones | Rm 483 | Portable Hip | 4/11/2010 11:22:48 AM |
| ● Bill Miller | Rm 508 | Portable Hip | 4/11/2010 11:23:37 AM |
| ● Bill Smith | Rm 572 | Knee | 4/11/2010 11:23:30 AM |
| ● Bill Miller | Rm 778 | Portable Chest | 4/11/2010 11:23:16 AM |
| ● Mike Jones | Rm 884 | Knee | 4/11/2010 11:23:23 AM |
| ● Robert Jones | Rm 944 | Portable Hip | 4/11/2010 11:23:02 AM |
| ● Fred Johnson | Rm 993 | Knee | 4/11/2010 11:23:58 AM |

MOBILE RADIOGRAPHY UNIT HAVING SINGLE SIGN ON AND METHODS FOR USING THE SAME

CROSS REFERENCE TO RELATED APPLICATIONS

Priority is claimed from commonly assigned, U.S. provisional patent application Ser. No. 61/323,535, filed Apr. 13, 2010, entitled "MOBILE UNIT HAVING SINGLE SIGN ON", in the name of Michael C. Lalena, the disclosure of which is incorporated by reference.

FIELD OF THE INVENTION

The invention relates generally to the field of medical imaging, and in particular to portable radiographic imaging apparatus. More specifically, the invention relates to a mobile radiography apparatus having multiple controls or capabilities requiring secured access.

BACKGROUND

Mobile carts are employed in medical facilities to move medical equipment between locations. One type of mobile cart includes an x-ray source used to capture (e.g., digital) x-ray images on x-ray detector. Medical x-ray images can be captured using various digital or analog techniques.

Refer also to U.S. Pat. No. 7,611,282 (Koren) and WO 2007/139638 (Jadrich), and WO 2007/078684 (Dhurjaty), and U.S. Pat. No. 5,844,961 (McEvoy).

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in mobile x-ray apparatus design to allow such devices to be more easily transported, deployed and/or operated.

SUMMARY OF THE INVENTION

An aspect of this application is to advance the art of mobile radiography.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which mobile radiography carts can be modified to use a single secure access apparatus and/method to control at least two of (i) a transport mechanism, (ii) x-ray generator control, (iii) remote detector control and image processing control, or (iv) secured storage for at least one radiographic detector.

Another aspect of the application is to provide methods and/or apparatus by which mobile radiography carts can use a single secure access to select and/or control (i) an operator selectable mobile radiography cart transport speed, or (ii) an operator selectable mobile radiography cart operational speed.

Another aspect of the application is to provide methods and/or apparatus by which mobile radiography carts can be modified to use a single secure access apparatus and/method to control (i) a transport mechanism, (ii) x-ray generator control, (iii) remote detector control and image processing control, or (iv) secured storage for at least one radiographic detector and a second secured access apparatus to control (i) a transport mechanism and (ii) x-ray generator control.

Another aspect of the application is to provide methods and/or apparatus by which mobile radiography carts can be modified to use a single secure access apparatus and/method to control (i) a transport mechanism, (ii) x-ray generator control, (iii) remote detector control and image processing control, or (iv) secured storage for at least one radiographic detector and a second secured access apparatus to control only a transport mechanism.

In accordance with one embodiment, the present invention can provide a mobile radiography apparatus that can include a moveable transport frame; a lockable drive mechanism configure to transport the moveable transport frame; a handle coupled to the moveable transport frame; an adjustable support structure coupled to the moveable transport frame; an x-ray source coupled to the adjustable support structure; a first display to provide control of at least one remote digital detector; a control unit configured to provide control of the x-ray source; a lockable storage control configured to lockably store the at least one remote digital detector at the mobile x-ray radiography apparatus; and a single access controller, responsive to a single verifiable identification, configured to integrate access control to the first display, the control unit, the lockable storage control and the lockable drive mechanism.

In accordance with one embodiment, the present invention can provide a method for operating a portable x-ray radiography apparatus, the method can include providing a moveable transport frame; providing a lockable drive mechanism configure to transport the moveable transport frame; providing a handle coupled to the moveable transport frame; providing an adjustable support structure coupled to the moveable transport frame; providing an x-ray source; providing a first display to provide control of at least one remote digital detector; providing a control unit configured to provide control x-ray source; providing a lockable storage control configured to lockably store the at least one remote digital detector at the mobile x-ray radiography apparatus; and providing a single access controller, responsive to a single verifiable identification, configured to integrate access control to the first display, the control unit, the lockable storage control and the lockable drive mechanism.

In accordance with one embodiment, the present invention can provide a mobile radiography apparatus that can include a moveable transport frame; a lockable drive mechanism configure to transport the moveable transport frame; an adjustable support structure coupled to the moveable transport frame; an x-ray source coupled to the adjustable support structure; a first display to provide control of at least one remote digital detector; a control unit configured to provide control of the x-ray source; and a single access controller, responsive to a single verifiable identification, configured to integrate access control to the first display, the control unit, and the lockable drive mechanism.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DESCRIPTION OF EXEMPLARY EMBODIMENTS

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Figure 1:
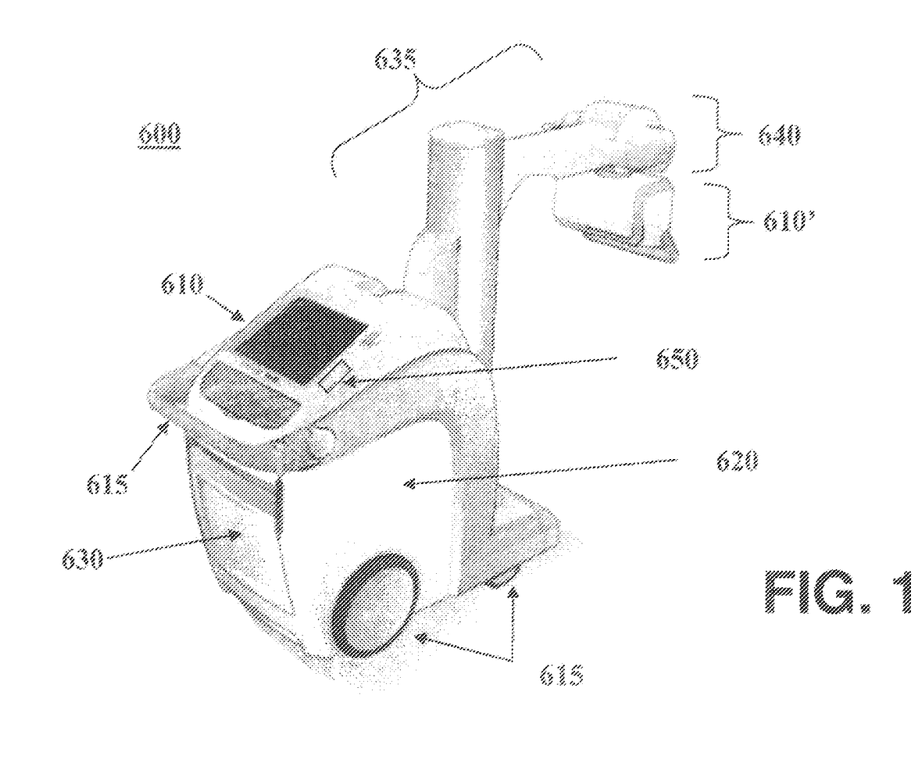
FIG. 1 is a diagram that shows a perspective view of a mobile radiography unit with a second display according to one embodiment of the application.

FIG. 1 is a diagram that shows a perspective view of a mobile radiography unit capable of single sign on according to embodiments of the application. The exemplary mobile x-ray or radiographic apparatus of FIG. 1 can be employed for computed radiography (CR) and/or digital radiography (DR). As shown in FIG. 1, a mobile radiography apparatus 600 can include a moveable transport frame 620 that includes a first display 610 and an optional second display 610' for display relevant information such as obtained images and related data. As shown in FIG. 1, the second display 610' can be pivotable mounted at the x-ray source 640 to be viewable/touchable from a 360 degree area around the tube head.

The displays 610, 610' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 600 can have one or more wheels 615 and one or more handle grips 625, typically provided at waist-level, arm-level, or hand-level, that help to guide the mobile radiographic apparatus 600 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 600 can include an area/holder for holding/storing one or more digital detectors or computed radiography cassettes. The area/holder can be storage area 630 (e.g., disposed on the frame 620) configured to removably retain at least one digital radiography (DR) detector. The storage area 630 can be configured to hold a plurality of detectors and can also be configured to hold one size or multiple sizes of DR detectors.

Mounted to frame 620 is a support column 635 that supports an x-ray source 640, also called an x-ray tube, tube head, or generator that can be mounted to the support column 635. In the embodiment shown in FIG. 1, the support column 635 can include a second section that extends outward a fixed/variable distance from a first section where the second section is configured to ride vertically up and down the first section to the desired height for obtaining the image. In another embodiment, the tube head or x-ray source 640 can be rotatably coupled to the support column 635. In another exemplary embodiment, an articulated member of the support column that bends at a joint mechanism can allow movement of the x-ray source 640 over a range of vertical and horizontal positions. Height settings for the x-ray source 640 can range from low height for imaging feet and lower extremities to shoulder height and above for imaging the upper body portions of patients in various positions.

Figure 2:
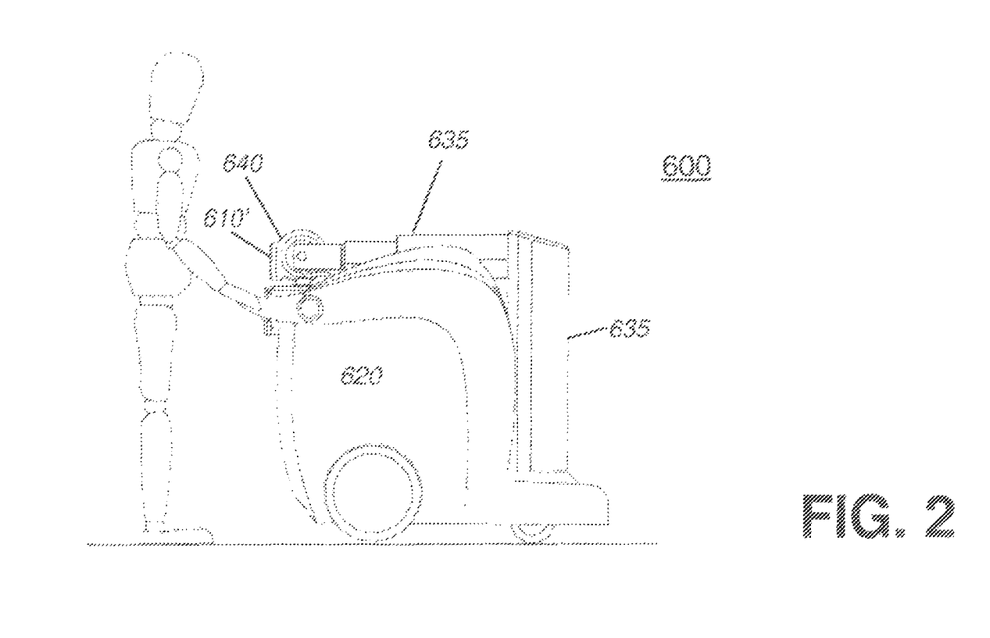
FIG. 2 is a diagram that shows a perspective view of a mobile radiography unit of FIG. 1 positioned for travel.

As shown in FIG. 2, for ease during transport of the mobile radiographic apparatus 600, the support member 635 and x-ray source 640 can be arranged close to frame 620. As shown in FIG. 2, the second display 610' can be in a viewable position (e.g., operable) during transport of the mobile radiographic apparatus 600. In one embodiment, the first display 610 can be disabled during transport. When the mobile radiographic apparatus 600 is to be used, the support member 635 and x-ray source 640 can be extended from the frame 620 for proper positioning (e.g., by the operator, a user, or x-ray technician) and the second display 610' moved to viewable position as shown in FIG. 1.

Figure 3:
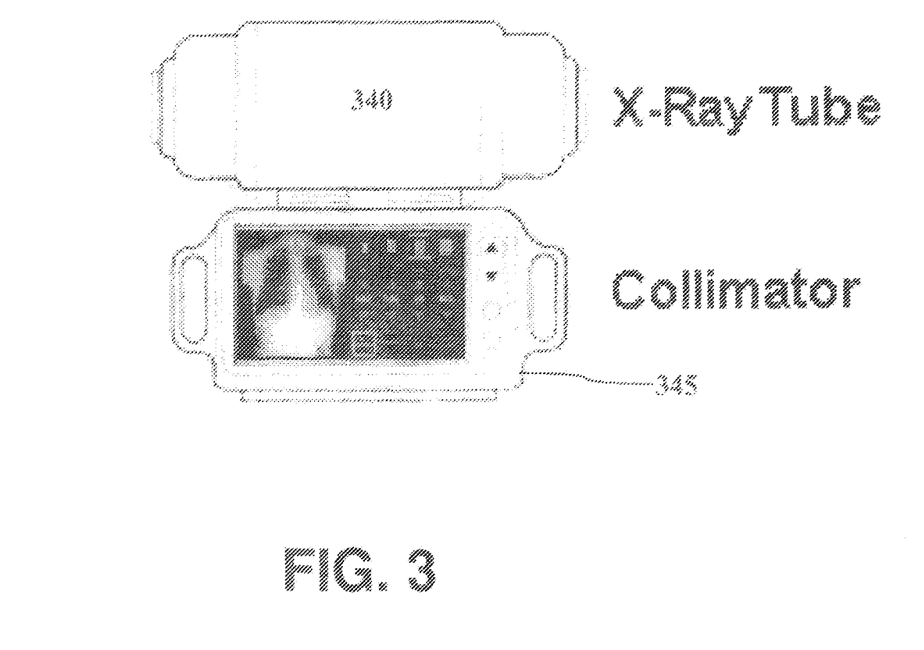
FIG. 3 is a diagram that shows an exemplary embodiment of a display/monitor as a second display mounted to a boom assembly of a mobile radiography unit according to the application.

FIG. 3 is a diagram that shows an exemplary embodiment of a display/monitor as a second display mounted to a boom assembly of a mobile radiography unit according to the application. As shown in FIG. 3, the second display 610' can be mounted to a collimator 345 of an x-ray source 340 of a boom assembly of a mobile radiography unit. "Boom assembly" can refer to the x-ray tube, a housing for the x-ray tube, a collimator, a structure/box below the collimator used to achieve (for example, 30 cm) separation between the tube and the patient, or any portion of the adjustable support column that can be used to position the tube over the patient. In one embodiment, the collimator 345 is rotably mounted to the x-ray source 340 so that the collimator 345 (e.g., second display 610') can swivel at least 90 degrees, at least 180 degrees or 360 degrees. As shown in FIG. 3, the second display 610' is coupled to a plurality of handles for ease of positioning. Alternatively, the second display 610' can be mounted to (e.g., rotatably) an x-ray source 340 above a collimator 345 of a boom assembly of a mobile radiography unit.

According to exemplary embodiments of the application, the first display 610 and the second display 610' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 610 and the second display 610' can provide capabilities/functionality to the mobile x-ray imaging apparatus 600 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam (In one embodiment, such a patient worklist can be automatically updated (e.g., synchronized to a master/hospital/doctor worklist) using a wired or wireless network/connection. In one embodiment, the mobile x-ray imaging apparatus 600 can highlight/indicate new exams (e.g., on the second display 610') upon receipt of the scheduled examination); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile x-ray imaging apparatus 600 during transport, e.g., using a video camera located on the other side (e.g., front side of the mobile x-ray imaging apparatus 600).

Related art mobile x-ray carts can include a first sign-on to main console (e.g., single display) on the transport frame to control operations of the x-ray generator/source and a second sign-on (e.g., key) to access a transport function of the mobile x-ray carts. Alternatively, related art mobile x-ray carts can include a first sign-on to main console (e.g., single display) on the transport frame to view/modify images captured using the x-ray source and a second sign-on (e.g., key) to access the control operations of the x-ray generator/source and/or the transport function of the mobile x-ray carts. Further, when locked, for example in an intensive care room, outside a patient room or emergency situation, a custodian, another technician, a doctor, a nurse and/or medical personnel does not have the ability to move the locked related art mobile x-ray apparatus.

Embodiments of methods and/or apparatus by which mobile radiography carts can be modified to use a single secure access apparatus and/or methods to control at least two of (i) a transport mechanism, (ii) x-ray generator control, (iii) remote detector control and image processing control, or (iv) secured storage for at least one radiographic detector.

Embodiments according to the application are directed to a single sign-on capability for portable radiographic apparatus. Exemplary single sign-on embodiments can combine turning on (e.g., power on, key start) the portable radiographic apparatus and a computer login (e.g., main console or first display 610/second display 610') where the computer logon action can complete a transport mechanism enablement procedure, a x-ray generator/source control operations access, and/or a lockable storage for a plurality of detectors access.

Thus, in one embodiment, a single sign-on can be a single logon by an operator to activate a portable radiographic cart and a user interface by employing a single action. Once the operator has logged on (e.g., signed in) to the portable radiographic cart, the operator will be able to drive/move the cart, view images, take exposures, and all other operations provided/allowable to that operator.

Exemplary single sign-on embodiments can include but are not intended to be limited to a pin/password logon, a user name and a password logon, a card reader such as a smart card, a magnetic stripe card, bar code data, or a proximity reader compatible with access technologies such as RFID, bluetooth, wireless communication device, a proximity card, a wireless smart card, a wiegand card, a magnetic reader device/card, an optical reader device/card, an infrared reader device/card, or biometric data such as fingerprints, eye scan or the like.

Figure 4:
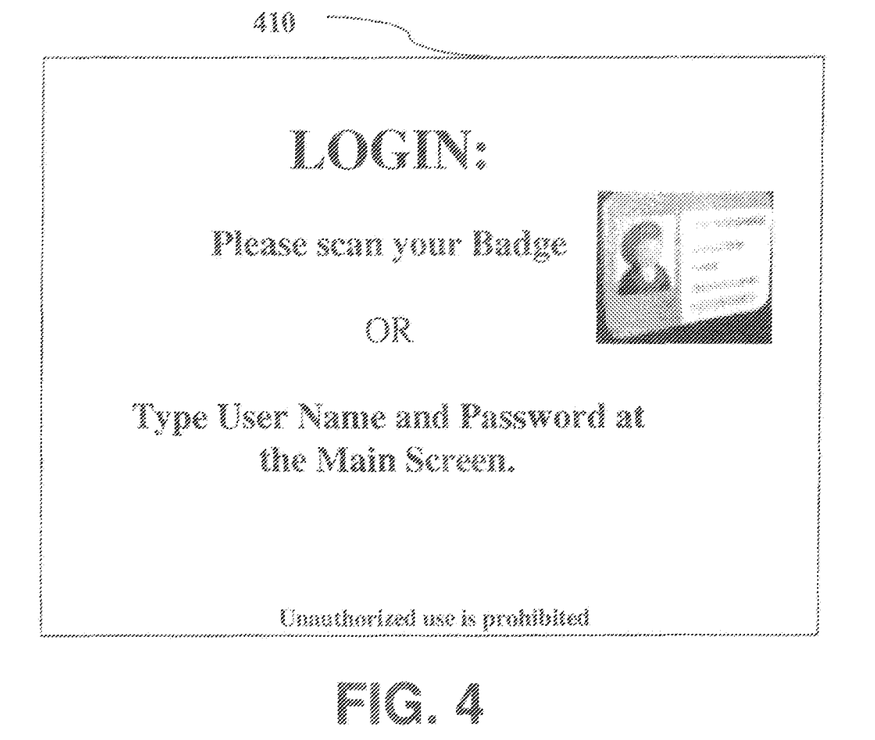
FIG. 4 is a diagram that illustrates an embodiment of a single sign on screen according to the application.

FIG. 4 is a diagram that illustrates an embodiment of a single sign on screen according to the application. Thus, when an attempt is made to operate the mobile x-ray imaging apparatus 600, a single sign on screen 410 can be displayed to provide instructions to a user. As shown in FIG. 4, the single sign on screen 410 can provide instructions for single sign on such as LOGIN: Please scan your badge or type User Name and Password at the main screen. Preferably, single sign on passwords can expire monthly and thereby be renewed for additional security. In addition, an unauthorized use warning can be displayed.

In one embodiment, a technician can use their ID badge to perform the single sign on to the mobile radiographic system 600 by placing their ID badge in close proximity to a single sign on reader 650. Verified identification using the single sign on reader 650 can provide authorization to access the first display 610 (and the optional second display 610'), access the lockable storage 630, access the drive mechanism using wheels 615 (e.g., a driving mechanism on the handle can be enabled) and access to controls for the tube head 640 including the x-ray source. Further, security features for control of single sign-on authorizations can be managed using an embodiment of a security authorization screen that can be accessed from a main screen on the first display 610 or the second display 610'.

Figure 5:
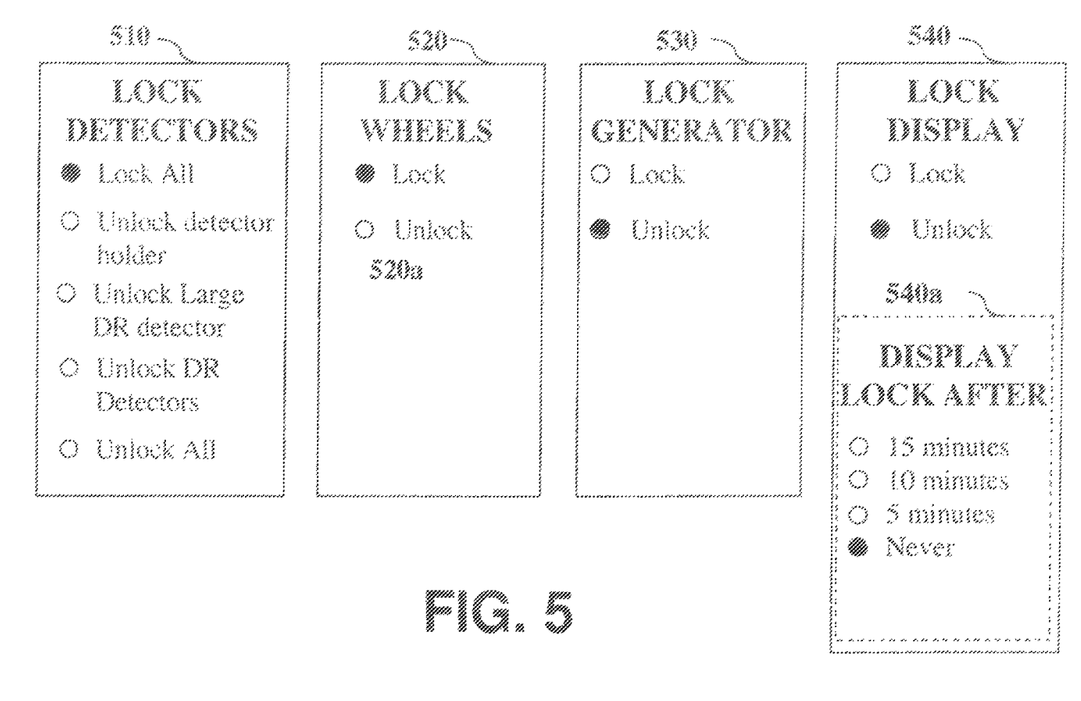
FIG. 5 is a diagram that illustrates an embodiment of a security authorization screen according to the application.

FIG. 5 is a diagram that illustrates an embodiment of a security authorization screen according to the application. As shown in FIG. 5, a security authorization screen can include a lockable storage selection 510, a lockable transport selection 520, a lockable x-ray source selection 530 and/or a lockable console selection 540. The lockable storage selection 510 can provide the operator with the capability of controlling access to one or more portable detectors to be carried on the mobile x-ray imaging apparatus 600. The lockable storage selection 510 can provide controllable access to the lockable storage bin 630. In one embodiment, the lockable storage bin 630 can have an open position allowing access to the DR detectors that can be individually locked/unlocked for secured access. In the open position, the lockable storage bin 630 can have multiple sized lockable individual detector holders. The lockable transport selection 520 can provide the operator with the capability of locking the mobile x-ray imaging apparatus 600. In one embodiment, the single sign on capability can allow for a custodian or medical personnel to scan their ID badge, and when authorized by positive identify verification, allow a manual movement of the mobile x-ray imaging apparatus 600. In another embodiment, a verified secondary sign-on using the single sign on reader 650 can be an access code entered through a keypad at the first display 610, which can unlock the transport mechanism (e.g., wheels) only. Such a limited functionality provided by a verified secondary sign-on by the single sign on reader 650 can allow for secured, but limited access to the mobile x-ray imaging apparatus 600 in a medical facility when needed (e.g., and emergency, a fire). The lockable generator selection 530 can provide the operator with the capability of controlling access to radiographic source of the mobile x-ray imaging apparatus 600. The lockable x-ray source selection 530 can provide the operator with the capability of controlling access to one or more portable detectors to be carried on the mobile x-ray imaging apparatus 600. The lockable console selection 540 can provide the operator with the capability of controlling access to main console (e.g., first display 610) of the mobile x-ray imaging apparatus 600. Further, the lockable console selection 540 can provide a secured sleep mode 540a whereby the first display 610 is locked after a set time interval (e.g., variable) of inactivity.

Related art mobile x-ray carts can include a first higher or peak speed when the cart is in transport (e.g., the support member 635 is in a locked position) and a second lower speed when the cart is not in transport. When a mobile x-ray cart is to be transported long distances, the mobile x-ray cart operator will set the mobile x-ray cart to its' top speed or peak speed position (e.g., compress the cart drive handle). The related art mobile x-ray cart transport speed and the in-use speed are set as maximum speeds. For example, the related art mobile x-ray cart maximum speeds can be set using a wheel driving mechanism. However, the peak drive speed of the related art mobile x-ray carts does not necessarily match a complete demographic spectrum of technicians/operators comfortable walking speeds. Thus, a first operator may need to walk too quickly to keep up with the related art mobile x-ray cart, while a second operator can find the speed is too slow and kick the rear of the cart with each stride.

Exemplary apparatus and/or method embodiments according to the application can provide a capability for a mobile x-ray apparatus 600 operator to select a first speed (e.g., transport speed) and to select a second speed (e.g., operational speed). Embodiments according to the application can provide the capability for the operator to save their desired peak cart speed under a personal identification code or personnel identification (e.g., ID badge). Thus, embodiments can be used with a proximity ID badge reader and the single sign on reader 650. When an operator swipes their proximity badge, the saved peak speeds (e.g., transport profile) can be loaded as the current speeds for the mobile x-ray apparatus 600.

Figure 6:
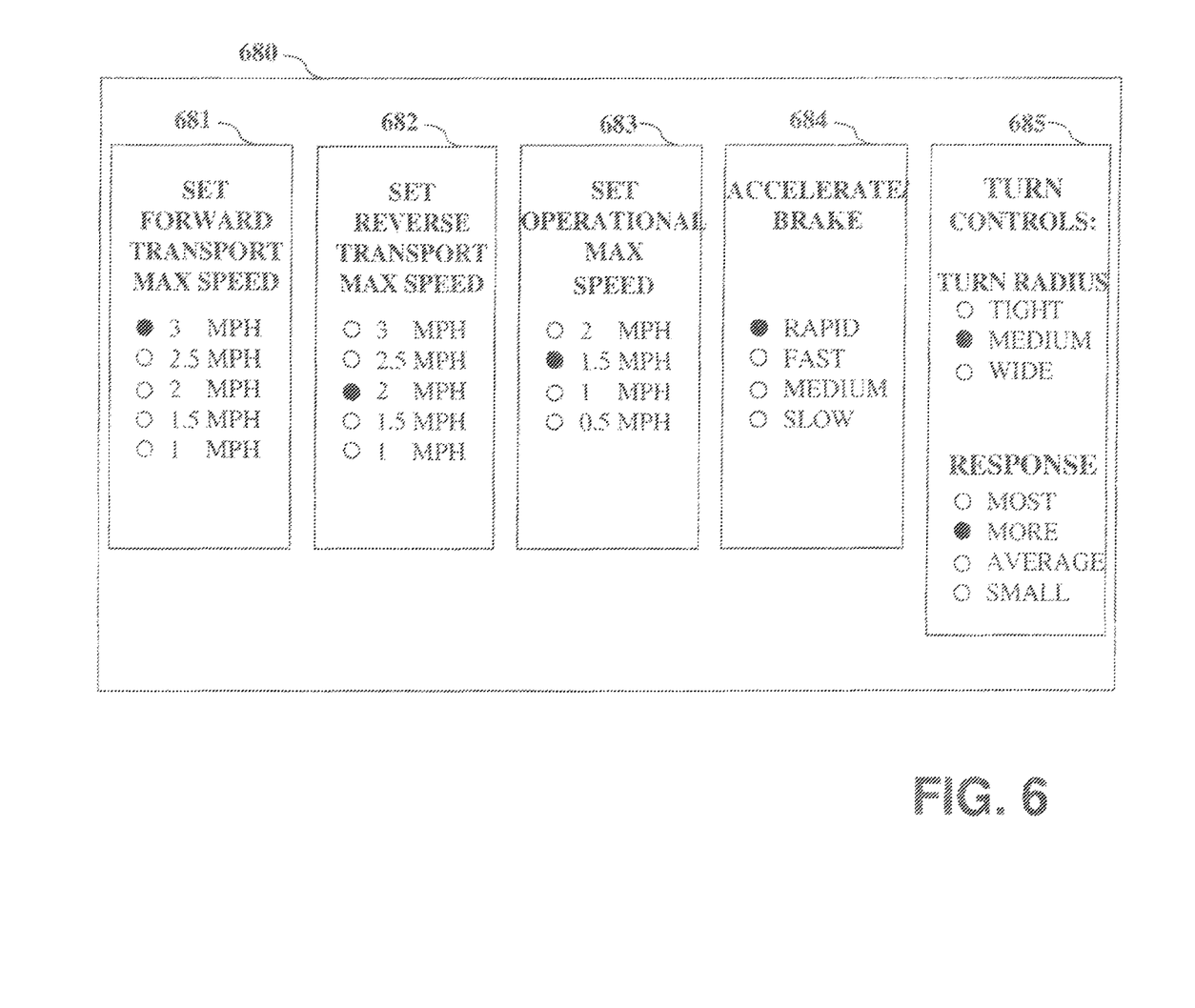
FIG. 6 is a diagram that illustrates an embodiment of a user profile screen according to the application.

In one embodiment, when the tube head 640 is locked or docked in a travel configuration (e.g., FIG. 2), the mobile x-ray apparatus 600 can have a first top speed (e.g., walking speed) and when the tube head 640 is moved away from the locked configuration (e.g., unlocked, FIG. 1) the mobile x-ray apparatus 600 can have a second top speed (e.g., operational or positioning speed), where the second top speed is different or less than the first top speed. FIG. 6 is a diagram that illustrates an embodiment of a user profile screen according to the application. As shown in FIG. 6, a user profile screen 680 can include a set forward transport speed 681, a set reverse transport speed 682, and a set operational speed 683. Thus, each of the first top speed and the second top speed along with the reverse speed can be modified by the user in the exemplary user transport profile 680 and stored in the mobile x-ray apparatus 600. Further, when the tube head 640 is locked or docked in a travel configuration, the operator can view a worklist (e.g., FIG. 7) on the second display 610', select a patient from the worklist and navigate to that selected patient's scheduled examination. While the tube head 640 is docked, the first display 610 is preferably turned off.

The user profile screen 680 can also include additional user profile settings for accelerate/brake 684 transitions and turn controls 685. The accelerate/brake 684 can provide the operator to variable control a time to attain the forward and/or reverse speed. Thus, a slow setting for the accelerate/brake 684 will take longer to stop the mobile x-ray apparatus 600 than a rapid setting. As shown in FIG. 6, the turn controls include turn radius setting and a response setting where a "most" setting can abruptly or quickly implement a turn by the operator and a "small" response setting can sluggishly implement the turn.

Although the user profile screen 680 was implemented with selectable buttons, embodiments according to the application are not intended to be so limited. For example, the operator selections in the user profile screen 680 can be provided by controls such as but not limited to low/medium/high, select within a number range (e.g., between 1-10), a press an arrow to increase/fill a bar, a fillable graphic, a graphic that switches color, etc. so that each operator has control of a range of driving characteristics to suit each individual operator, which are remembered when the operator next signs-on the mobile x-ray apparatus 600.

In one embodiment, a site administrator (e.g., user with special privileges) for a medical facility or the like can be able to configure the transport speed (e.g., first or maximum MAX speed) and/or the operational speed that an operator of the mobile x-ray apparatus 600 can select. For example, although a top speed attainable by the mobile x-ray apparatus 600 can be 5 MPH (8.05 KPH), the site administer can set the top transport speed to 3 MPH (4.83 KPH), which can permit the individual operators to configure a transport speed 682 to be between 1-3 MPH (1.61-4.83 KPH). Further, the site administrator can set the speed range for the operational speed 684 of the mobile x-ray apparatus 600 selectable by the individual operators. In one embodiment, the site administrator can be and installation technician and the transport speed can be set in installation or repeatedly thereafter.

In one embodiment, the second display 610' can provide a back-up mode or "fail safe mode" so that in the event of a failure of the first display 610 or the console/PC/processor, which can control the first display 610, the second display 610' can operate to change exposure parameters and/or expose CR cassettes or expose x-ray film cassettes in a back-up capability or fail safe mode. Thus, the mobile radiographic apparatus 600 can perform x-ray exposures when either one of the first display 610 or the second display 610' are inoperable. Further, the single sign-on backup can be implemented at the second display 610' using a displayed keypad (or coupled input device) and verified identification (e.g., user ID and user password) to temporarily replace single sign on reader 650.

Figure 7:
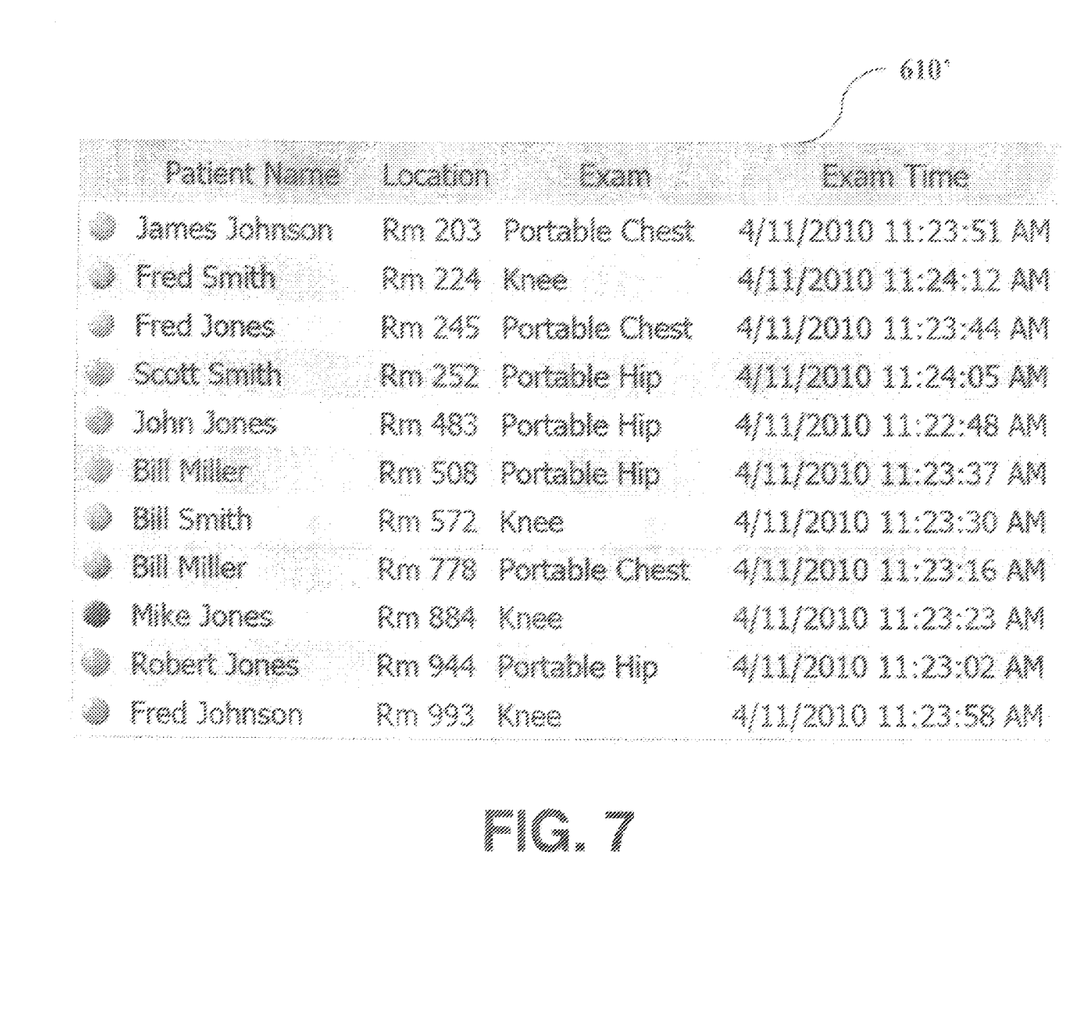
FIGS. 7-10 are diagrams that illustrate exemplary functions implemented at an embodiment of a second display of a mobile x-ray imaging apparatus.
Figure 8:
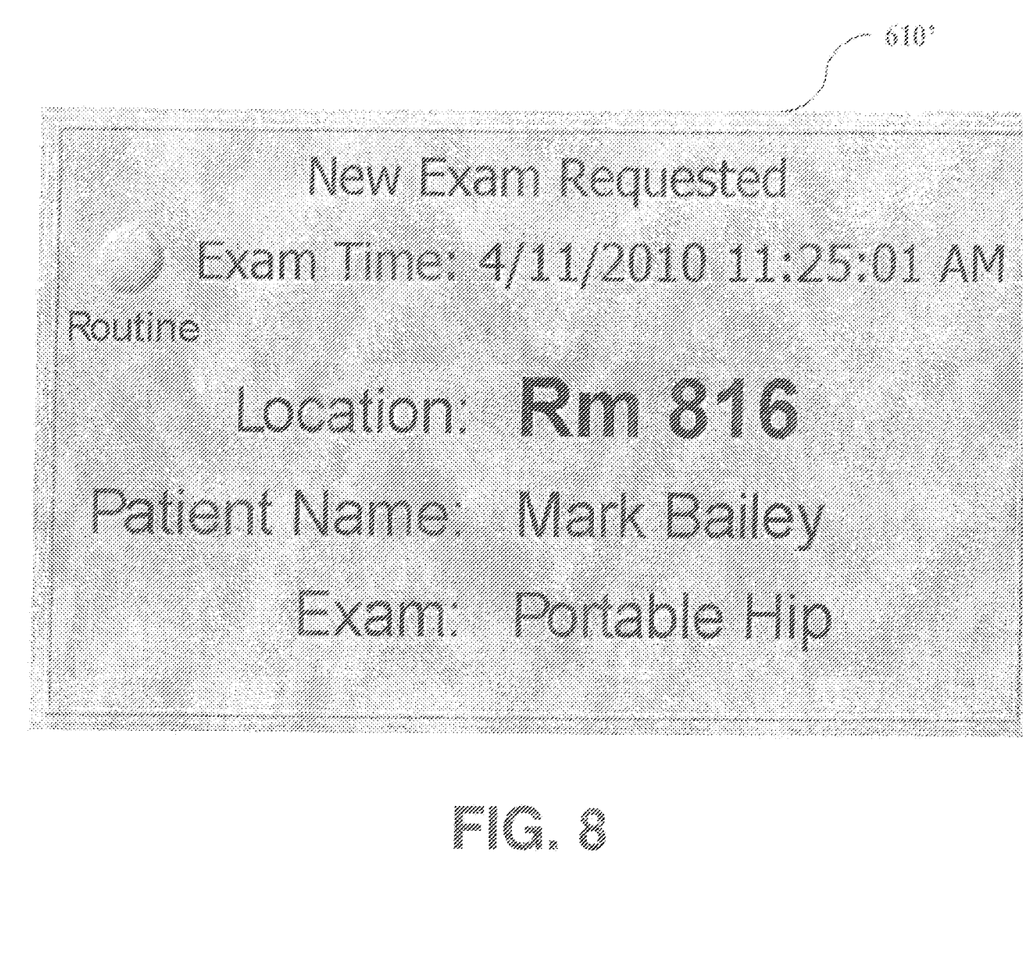
Figure 9:
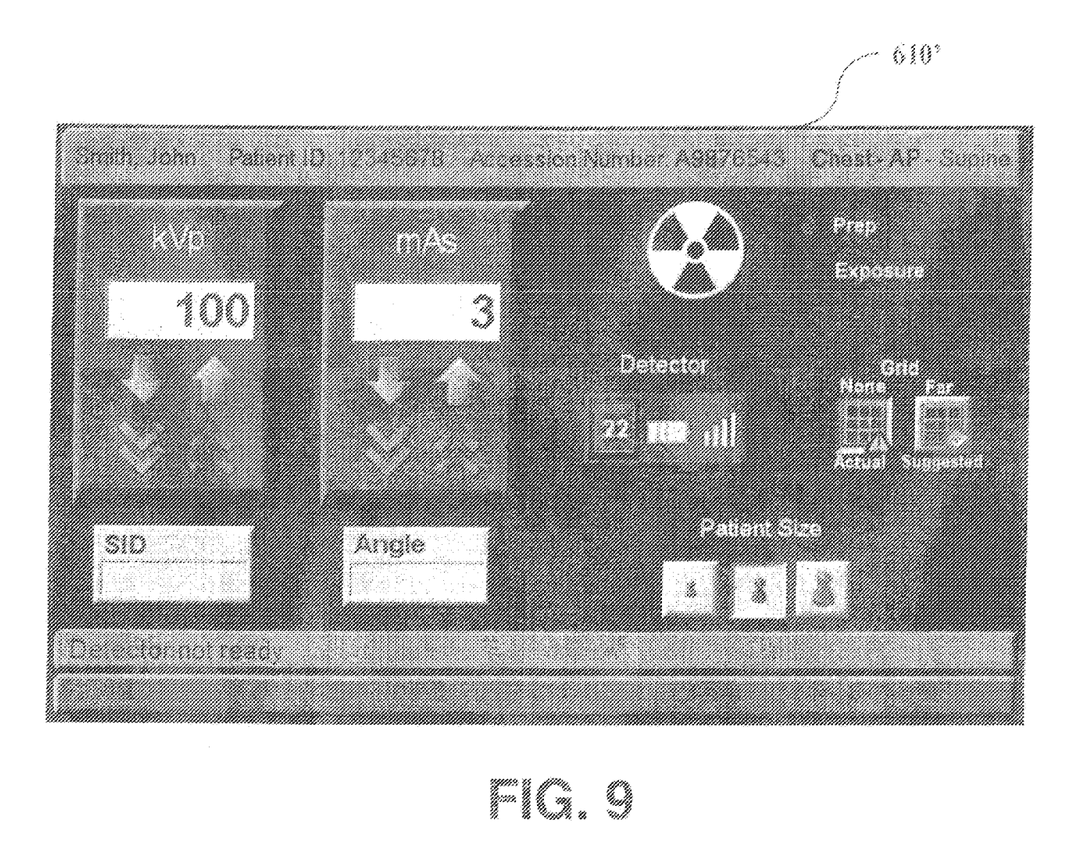
Figure 10:
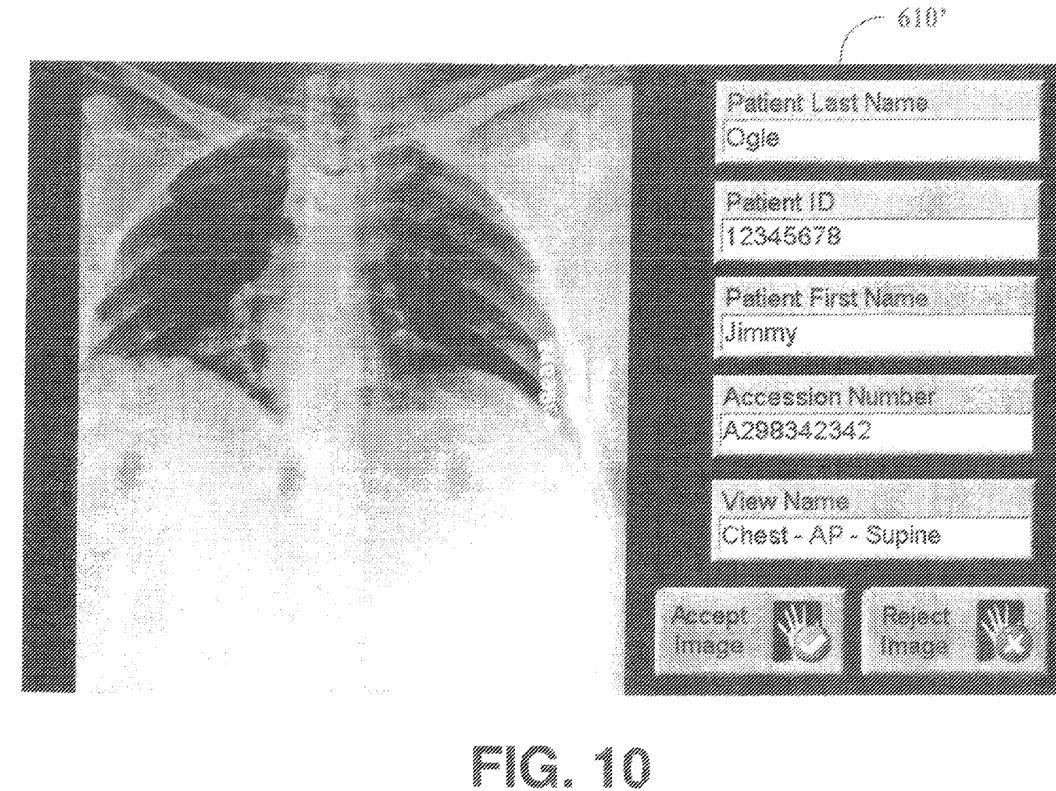

FIGS. 7-10 are diagrams that illustrate exemplary non-limiting representative functions illustrated on an embodiment of a second display of a mobile e-ray imaging apparatus. As shown in FIG. 7, an example of a work list is shown on a monitor of the second display 610'. As shown in FIG. 8, an example of a new examination/procedure information/requirement for that technician and/or patient is shown on a monitor of the second display 610'. As shown in FIG. 9, an example of x-ray source controls is shown on a monitor of the second display 610'. As shown in FIG. 10, an example of newly acquired image and patient information is shown on a monitor of the second display 610'.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments according to the application can provide various advantages including a mobile x-ray unit including a single sign on and/or selectable user profile information stored in connection with a verified operator.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile x-ray radiography apparatus comprising:
a moveable transport frame;
a lockable drive mechanism configured to transport the moveable transport frame;
a handle coupled to the moveable transport frame;
an adjustable support structure coupled to the moveable transport frame;
an x-ray source coupled to the adjustable support structure;
a first display to provide control of at least one remote digital detector;
a control unit configured to provide control of the x-ray source;
a lockable storage control configured to lockably store the at least one remote digital detector at the mobile x-ray radiography apparatus; and
a single access controller, responsive to a single verifiable identification, configured to integrate access control to the first display, the control unit, the lockable storage control and the lockable drive mechanism.

2. The mobile x-ray radiography apparatus of claim 1, further comprising a lockable storage unit controlled by the lockable storage control, the lockable storage unit configured to releasably secure the at least one remote digital detector when stored at the mobile x-ray radiography apparatus where the lockable storage unit is configured to provide selectable access to a plurality of detectors.

3. The mobile x-ray radiography apparatus of claim 2, where the lockable storage unit is configured to provide selectable access to a plurality of different sized DR detectors or a DR detector holder.

4. The mobile x-ray radiography apparatus of claim 1, where the single access controller is a proximity badge reader and the single access controller is enabled by placing an ID badge in operable range of the proximity badge reader.

5. The mobile x-ray radiography apparatus of claim 1, where the single access controller is an identification and password combination, a User Name and a password, combination, a pin and password combination, an identification reader including a RFID, a proximity card, a wiegand card, a wireless smart card, a smart card, a magnetic stripe card, a bar code data or biometric data.

6. The mobile x-ray radiography apparatus of claim 1, where the single access controller is configured to provide a second single sign-on capability at the mobile x-ray radiography apparatus, the second single sign-on capability to control only the lockable drive mechanism.

7. The mobile x-ray radiography apparatus of claim 6, wherein the second single sign-on capability is configured to allow additional facility personnel to move a locked mobile x-ray radiography apparatus.

8. The mobile x-ray radiography apparatus of claim 1, where the first display is configured to provide a user profile, where the user profile is configured to set by an operator selection of a transport speed among a transport speed range.

9. The mobile x-ray radiography apparatus of claim 8, where the user profile is stored with a corresponding single sign-on ID, and where the user profile is configured to select an operational speed among an operational speed range.

10. The mobile x-ray radiography apparatus of claim 8, where the transport speed range is configured to be set by a corresponding administrator operator.

11. The mobile x-ray radiography apparatus of claim 1, comprising a second display, where the second display is configured to provide control of the x-ray source and the lockable drive mechanism, where the first display and the second display are respectively mounted to the movable transport frame or the adjustable support structure.

12. The mobile x-ray radiography apparatus of claim 11, wherein when the single access controller is disabled, the second display is configured to provide control of the x-ray source and the lockable drive mechanism to provide a failsafe capability to take exposures using the x-ray source by control of exposure parameters including kVp.

13. The mobile x-ray radiography apparatus of claim 11, where the first display and the second display are each configured to display obtained images and related data and a control panel to allow functions including at least one of storing, transmitting, modifying, and printing of the obtained images, where the first display and the second display are each configured to view or modify x-ray exposure parameters, or modify generator, source, or technique settings, display image information, display patient information, display a patient worklist, display generator current values and controls to change those values, display detector selection, allow the user to select or activate a different detector, display recently acquired images and allow editing of those images, indicators or imaging procedure information.

14. The mobile x-ray radiography apparatus of claim 1, where the adjustable support structure is configured to be adjustable in two dimensions or adjustable in three dimensions relative to the moveable transport frame, where the first display is rotable in a horizontal plane, rotatable in a vertical plane or rotatable both horizontally and vertically, and where the first display pivotably mounted to the adjustable support structure or the first display is rotable around the tube head or the adjustable support structure.

15. The mobile x-ray radiography apparatus of claim 1, where the first display provides an indication of location of the at least one remote digital detector when the at least one remote digital detector is assigned to the mobile x-ray radiography apparatus.

16. A method for operating a portable x-ray radiography apparatus, the method comprising:
providing a moveable transport frame;
providing a lockable drive mechanism configured to transport the moveable transport frame;
providing a handle coupled to the moveable transport frame;
providing an adjustable support structure coupled to the moveable transport frame;
providing a first display to provide control of at least one remote digital detector;
providing a control unit configured to provide control of a x-ray source;
providing a lockable storage control configured to lockably store the at least one remote digital detector at the mobile x-ray radiography apparatus; and
providing a single access controller, responsive to a single verifiable identification, configured to integrate access control to the first display, the control unit, the lockable storage control and the lockable drive mechanism.

17. A mobile x-ray radiography apparatus comprising:
a moveable transport frame;
a lockable drive mechanism configured to transport the moveable transport frame;
an adjustable support structure coupled to the moveable transport frame;
an x-ray source coupled to the adjustable support structure;
a first display to provide control of at least one remote digital detector;
a control unit configured to provide control of the x-ray source; and
a single access controller, responsive to a single verifiable identification, configured to integrate access control to the first display, the control unit, and the lockable drive mechanism.

18. The mobile x-ray radiography apparatus of claim 17, where the single access controller is a proximity badge reader and the single access controller is enabled by placing an ID badge in operable range of the proximity badge reader.

19. The mobile x-ray radiography apparatus of claim 17, where the single access controller is configured to provide a second single sign-on capability at the mobile x-ray radiography apparatus, the second single sign-on capability to control only the lockable drive mechanism.

20. The mobile x-ray radiography apparatus of claim 17, where the first display provides an indication of location of the at least one remote digital detector when the at least one remote digital detector is assigned to the mobile x-ray radiography apparatus, where the first display is configured to provide a user profile, where the user profile is configured to set by an operator selection of a transport speed among a transport speed range.

* * * * *

UNITED STATES PATENT AND TRADEMARK OFFICE
CERTIFICATE OF CORRECTION

| | |
|---|---|
| PATENT NO. | : 8,678,648 B2 |
| APPLICATION NO. | : 13/084907 |
| DATED | : March 25, 2014 |
| INVENTOR(S) | : Michael C. Lalena et al. |

It is certified that error appears in the above-identified patent and that said Letters Patent is hereby corrected as shown below:

In the Claims

Column 10, Line 51-52, Claim 13    Please replace "x-ray exposure parameters, or modify generator" with --x-ray exposure parameters, view or modify generator--

Signed and Sealed this
Twenty-fourth Day of February, 2015

Michelle K. Lee
*Deputy Director of the United States Patent and Trademark Office*